(12) United States Patent
Roorda

(10) Patent No.: US 9,055,932 B2
(45) Date of Patent: Jun. 16, 2015

(54) SUTURE FASTENER COMBINATION DEVICE

(75) Inventor: Wouter E. Roorda, Palo Alto, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 127 days.

(21) Appl. No.: 13/219,004

(22) Filed: Aug. 26, 2011

(65) Prior Publication Data

US 2013/0053884 A1 Feb. 28, 2013

(51) Int. Cl.
*A61B 17/04* (2006.01)
*A61B 17/00* (2006.01)

(52) U.S. Cl.
CPC ......... *A61B 17/0057* (2013.01); *A61B 17/0401* (2013.01); *A61B 2017/0414* (2013.01); *A61B 2017/0458* (2013.01); *A61B 17/0467* (2013.01); *A61B 17/0487* (2013.01); *A61B 2017/00004* (2013.01); *A61B 2017/00663* (2013.01); *A61B 2017/0088* (2013.01); *A61B 2017/00889* (2013.01); *A61B 2017/0404* (2013.01); *A61B 2017/0409* (2013.01); *A61B 2017/0454* (2013.01); *A61B 2017/0462* (2013.01); *A61B 2017/0474* (2013.01); *A61B 2017/0488* (2013.01)

(58) Field of Classification Search
USPC ......... 606/139, 144, 148, 151, 213, 215, 216, 606/217, 232; 24/127, 128, 129 D; 411/511, 411/512, 518
See application file for complete search history.

(56) References Cited

U.S. PATENT DOCUMENTS

| | | | |
|---|---|---|---|
| 2,238,563 A | 4/1941 | Jacques | |
| 2,416,260 A | 2/1947 | Karle | |
| 2,449,235 A | 9/1948 | Krupp | |
| 3,766,610 A | 10/1973 | Thorsbakken | |
| 3,877,434 A | 4/1975 | Ferguson et al. | |
| 4,156,574 A | 5/1979 | Boden | |
| 4,705,040 A | 11/1987 | Mueller et al. | |
| 4,750,492 A | 6/1988 | Jacobs | |
| 4,807,333 A | 2/1989 | Boden | |
| 5,292,332 A | 3/1994 | Lee | |
| 5,342,393 A | 8/1994 | Stack | |
| 5,364,408 A | 11/1994 | Gordon | |
| 5,383,905 A | 1/1995 | Golds et al. | |
| 5,417,699 A | 5/1995 | Klein et al. | |
| 5,435,044 A | 7/1995 | Ida | |
| 5,454,140 A | 10/1995 | Murai | |
| 5,462,558 A | 10/1995 | Kolesa et al. | |
| 5,478,353 A | 12/1995 | Yoon | |

(Continued)

FOREIGN PATENT DOCUMENTS

| | | |
|---|---|---|
| WO | WO 02/15795 | 2/2002 |
| WO | WO 2005/027754 | 3/2005 |

OTHER PUBLICATIONS

U.S. Appl. No. 13/022,246, Nov. 28, 2012, Office Action.

(Continued)

*Primary Examiner* — Dianne Dornbusch
*Assistant Examiner* — Robert Lynch
(74) *Attorney, Agent, or Firm* — Workman Nydegger; Randy Shen

(57) ABSTRACT

A closure system for closing openings in tissue that includes a closure device and a fastener. The closure device includes shafts that are configured to deploy a fastener to close an opening in tissue. The closure device can deploy the fastener as a knot pusher to close the opening with sutures or as a knot replacement to close the opening with sutures.

20 Claims, 7 Drawing Sheets

(56) References Cited

U.S. PATENT DOCUMENTS

| | | | |
|---|---|---|---|
| 5,501,692 A | 3/1996 | Riza | |
| 5,507,754 A | 4/1996 | Green et al. | |
| 5,520,070 A | 5/1996 | Beugelsdyk et al. | |
| 5,520,702 A | 5/1996 | Sauer et al. | |
| 5,562,688 A | 10/1996 | Riza | |
| 5,562,689 A | 10/1996 | Green et al. | |
| 5,569,306 A | 10/1996 | Thai | |
| 5,572,770 A | 11/1996 | Boden | |
| 5,575,800 A | 11/1996 | Gordon | |
| 5,584,861 A | 12/1996 | Swain et al. | |
| 5,613,974 A * | 3/1997 | Andreas et al. | 606/144 |
| 5,630,824 A | 5/1997 | Hart | |
| 5,645,553 A | 7/1997 | Kolesa et al. | |
| 5,658,313 A | 8/1997 | Thal | |
| 5,662,664 A | 9/1997 | Gordon et al. | |
| 5,700,272 A | 12/1997 | Gordon et al. | |
| 5,702,397 A | 12/1997 | Goble et al. | |
| 5,725,529 A | 3/1998 | Nicholson et al. | |
| 5,779,707 A | 7/1998 | Bertholet et al. | |
| 5,868,762 A | 2/1999 | Cragg et al. | |
| 5,893,856 A | 4/1999 | Jacob et al. | |
| 5,902,311 A | 5/1999 | Andreas et al. | |
| 5,941,901 A | 8/1999 | Egan | |
| 6,086,608 A | 7/2000 | Ek et al. | |
| 6,099,547 A | 8/2000 | Gellman et al. | |
| 6,136,010 A | 10/2000 | Modesitt et al. | |
| 6,190,414 B1 | 2/2001 | Young et al. | |
| 6,200,329 B1 | 3/2001 | Fung et al. | |
| 6,203,554 B1 | 3/2001 | Roberts | |
| 6,206,895 B1 | 3/2001 | Levinson | |
| 6,228,096 B1 | 5/2001 | Marchand | |
| 6,231,592 B1 | 5/2001 | Bonutti et al. | |
| 6,245,080 B1 | 6/2001 | Levinson | |
| 6,277,140 B2 | 8/2001 | Ginn et al. | |
| 6,398,796 B2 | 6/2002 | Levinson | |
| 6,712,837 B2 | 3/2004 | Akerfeldt et al. | |
| 6,746,457 B2 | 6/2004 | Dana et al. | |
| 6,786,915 B2 | 9/2004 | Akerfeldt et al. | |
| 7,011,400 B2 | 3/2006 | Nakano | |
| 7,033,370 B2 | 4/2006 | Gordon et al. | |
| 7,060,077 B2 | 6/2006 | Gordon et al. | |
| 7,147,646 B2 | 12/2006 | Dana et al. | |
| 7,320,693 B2 | 1/2008 | Pollack et al. | |
| 7,361,183 B2 | 4/2008 | Ginn | |
| 7,390,328 B2 | 6/2008 | Modesitt | |
| 7,435,251 B2 | 10/2008 | Green | |
| 7,662,161 B2 | 2/2010 | Briganti et al. | |
| 7,713,284 B2 | 5/2010 | Crofford | |
| 7,842,051 B2 | 11/2010 | Dana et al. | |
| 7,875,043 B1 | 1/2011 | Ashby et al. | |
| 7,931,670 B2 | 4/2011 | Fiehler et al. | |
| 7,947,062 B2 | 5/2011 | Chin et al. | |
| 8,048,108 B2 | 11/2011 | Sibbitt, Jr. et al. | |
| 8,100,923 B2 | 1/2012 | Paraschac et al. | |
| 8,128,652 B2 | 3/2012 | Paprocki | |
| 8,128,653 B2 | 3/2012 | McGuckin, Jr. et al. | |
| 8,262,736 B2 | 9/2012 | Michelson | |
| 8,337,522 B2 | 12/2012 | Ditter | |
| 8,480,691 B2 | 7/2013 | Dana et al. | |
| 8,579,934 B2 | 11/2013 | Ginn | |
| 8,647,364 B2 | 2/2014 | Fiehler et al. | |
| 8,932,324 B2 | 1/2015 | Sibbitt, Jr. et al. | |
| 8,932,327 B2 | 1/2015 | Kosa et al. | |
| 8,945,180 B2 | 2/2015 | Roorda | |
| 2001/0023352 A1 | 9/2001 | Gordon et al. | |
| 2001/0044638 A1 | 11/2001 | Levinson et al. | |
| 2001/0044639 A1 | 11/2001 | Levinson | |
| 2002/0002401 A1 | 1/2002 | McGuckin, Jr. et al. | |
| 2002/0077658 A1 | 6/2002 | Ginn | |
| 2002/0082641 A1 | 6/2002 | Ginn et al. | |
| 2002/0107542 A1 | 8/2002 | Kanner et al. | |
| 2002/0151921 A1 | 10/2002 | Kanner et al. | |
| 2002/0169478 A1 | 11/2002 | Schwartz et al. | |
| 2002/0188318 A1 | 12/2002 | Carley et al. | |
| 2003/0093096 A1 | 5/2003 | McGuckin, Jr. et al. | |
| 2003/0144695 A1 | 7/2003 | McGuckin, Jr. et al. | |
| 2003/0167062 A1 | 9/2003 | Gambale et al. | |
| 2003/0195514 A1 | 10/2003 | Trieu et al. | |
| 2003/0199987 A1 | 10/2003 | Berg et al. | |
| 2004/0093024 A1 | 5/2004 | Lousararian et al. | |
| 2004/0122451 A1 | 6/2004 | Wood | |
| 2004/0158309 A1 | 8/2004 | Wachter et al. | |
| 2005/0038500 A1 | 2/2005 | Boylan et al. | |
| 2005/0085853 A1 | 4/2005 | Forsberg et al. | |
| 2005/0096697 A1 | 5/2005 | Forsberg et al. | |
| 2005/0205640 A1 * | 9/2005 | Milliman | 227/176.1 |
| 2006/0190037 A1 | 8/2006 | Ginn et al. | |
| 2006/0235505 A1 | 10/2006 | Oepen et al. | |
| 2006/0241579 A1 | 10/2006 | Kawaura et al. | |
| 2006/0265008 A1 | 11/2006 | Maruyama et al. | |
| 2006/0265010 A1 * | 11/2006 | Paraschac et al. | 606/232 |
| 2007/0010853 A1 | 1/2007 | Ginn et al. | |
| 2007/0060895 A1 | 3/2007 | Sibbitt, Jr. et al. | |
| 2007/0149987 A1 | 6/2007 | Wellman et al. | |
| 2007/0255317 A1 * | 11/2007 | Fanton et al. | 606/232 |
| 2007/0270904 A1 | 11/2007 | Ginn | |
| 2007/0276433 A1 | 11/2007 | Huss | |
| 2007/0276488 A1 | 11/2007 | Wachter et al. | |
| 2008/0065156 A1 | 3/2008 | Hauser et al. | |
| 2008/0114395 A1 | 5/2008 | Mathisen et al. | |
| 2008/0312740 A1 | 12/2008 | Wachter et al. | |
| 2009/0012537 A1 | 1/2009 | Green | |
| 2009/0069847 A1 | 3/2009 | Hashiba et al. | |
| 2009/0157102 A1 | 6/2009 | Reynolds et al. | |
| 2009/0306671 A1 | 12/2009 | McCormack et al. | |
| 2009/0306685 A1 | 12/2009 | Fill | |
| 2010/0042144 A1 | 2/2010 | Bennett | |
| 2010/0179589 A1 * | 7/2010 | Roorda et al. | 606/213 |
| 2010/0179590 A1 | 7/2010 | Fortson et al. | |
| 2010/0256670 A1 | 10/2010 | Ginn et al. | |
| 2011/0029012 A1 * | 2/2011 | Tegels | 606/213 |
| 2012/0184991 A1 | 7/2012 | Paraschac et al. | |
| 2013/0046331 A1 | 2/2013 | Christensen et al. | |
| 2013/0103077 A1 | 4/2013 | Ditter | |
| 2013/0110165 A1 | 5/2013 | Burkhart et al. | |
| 2013/0218206 A1 | 8/2013 | Gadlage | |
| 2013/0296887 A1 | 11/2013 | Dana et al. | |
| 2013/0345745 A1 | 12/2013 | Kim | |
| 2014/0148824 A1 | 5/2014 | Fujisaki et al. | |
| 2014/0228868 A1 | 8/2014 | Hassan et al. | |
| 2014/0336702 A1 | 11/2014 | Rowe et al. | |
| 2014/0364904 A1 | 12/2014 | Kim | |

OTHER PUBLICATIONS

U.S. Appl. No. 12/917,195, Jun. 28, 2012, Office Action.
U.S. Appl. No. 13/022,246, May 11, 2012, Office Action.
U.S. Appl. No. 12/917,195, Aug. 1, 2012, Office Action.
U.S. Appl. No. 13/411,320, filed Mar. 2, 2012, Voss et al.
U.S. Appl. No. 12/684,470, filed Jan. 8, 2010, Voss et al.
U.S. Appl. No. 12/917,195, filed Nov. 1, 2010, Voss et al.
U.S. Appl. No. 13/022,246, filed Feb. 7, 2011, Yribarren.
U.S. Appl. No. 13/035,939, filed Feb. 26, 2011, Ehrenreich.
U.S. Appl. No. 13/022,246, Jun. 7, 2013, Office Action.
U.S. Appl. No. 13/035,939, Jan. 31, 2013, Office Action.
U.S. Appl. No. 60/502,925, filed Sep. 15, 2003, Paraschac.
U.S. Appl. No. 10/941,693, Nov. 17, 2006, Office Action.
U.S. Appl. No. 10/941,693, May 7, 2007, Office Action.
U.S. Appl. No. 10/941,693, Dec. 31, 2007, Office Action.
U.S. Appl. No. 10/941,693, Jul. 9, 2008, Office Action.
U.S. Appl. No. 10/941,693, Mar. 2, 2009, Office Action.
U.S. Appl. No. 10/941,693, Oct. 23, 2009, Office Action.
U.S. Appl. No. 10/941,693, Sep. 28, 2011, Notice of Allowance.
U.S. Appl. No. 11/460,863, Jul. 12, 2007, Office Action.
U.S. Appl. No. 11/460,863, Feb. 5, 2008, Office Action.
U.S. Appl. No. 11/460,863, Oct. 10, 2008, Office Action.
U.S. Appl. No. 11/460,863, Apr. 13, 2009, Office Action.
U.S. Appl. No. 12/917,195, May 6, 2013, Office Action.
U.S. Appl. No. 14/052,658, filed Oct. 11, 2013, Ehrenreich.
U.S. Appl. No. 12/917,195, Aug. 7, 2013, Notice of Allowance.
U.S. Appl. No. 13/035,939, Sep. 10, 2013, Office Action.
U.S. Appl. No. 13/022,246, Nov. 14, 2013, Notice of Allowance.

(56) References Cited

OTHER PUBLICATIONS

U.S. Appl. No. 13/035,939, Apr. 10, 2014, Office Action.
U.S. Appl. No. 13/035,939, Aug. 21, 2014, Office Action.
U.S. Appl. No. 13/356,129, May 6, 2014, Office Action.
U.S. Appl. No. 13/356,129, Sep. 15, 2014, Office Action.
U.S. Appl. No. 14/052,658, Sep. 4, 2014, Office Action.
U.S. Appl. No. 13/411,320, Feb. 3, 2015, Office Action.
U.S. Appl. No. 14/052,658, Mar. 27, 2015, Office Action.

* cited by examiner

SUTURE FASTENER COMBINATION DEVICE

BACKGROUND OF THE INVENTION

1. The Field of the Invention

Embodiments of the invention relate generally to medical devices. More particularly, embodiments of the invention relate to systems and methods for closing openings in tissue.

2. The Relevant Technology

Catheterization and interventional procedures, such as angioplasty or stenting, are generally performed through a patient's vascular system. These procedures often begin by inserting a hollow needle through the patient's skin and tissue into the vascular system. A guide wire may be advanced through the needle and into the patient's blood vessel accessed by the needle. The needle is then removed, enabling an introducer sheath to be advanced over the guide wire into the vessel, e.g., in conjunction with or subsequent to a dilator.

A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath are removed, leaving a puncture site or opening in the vessel wall. Traditionally, external pressure would be applied to the puncture site until clotting and wound sealing occur; however, the patient must remain bedridden for a substantial period after clotting to ensure closure of the opening. This procedure may be time consuming and expensive, requiring as much as an hour of a physician's or nurse's time. It is also uncomfortable for the patient and requires that the patient remain immobilized in the operating room, catheter lab, or holding area. In addition, a risk of hematoma exists from bleeding before hemostasis occurs.

Therefore, a need exists to close holes in tissue. There is also a need to provide physicians and nurses with options for closing holes or other openings in tissue.

BRIEF SUMMARY OF THE INVENTION

Embodiments of the invention relate to systems and methods for closing opening in tissue. Embodiments of the invention can close openings in tissue by operating as a knot pushing system or as a knot replacement system. A fastener included can either push a knot formed in sutures to close the opening or act as a knot replacement such that tying the knot is not required.

In one example, a closure system for closing an opening in tissue is provided. The closure system includes a fastener. The fastener includes an opening formed therein and sutures are received or drawn through the opening. The closure system also includes a closure device configured to deploy the fastener. The closure device includes an outer shaft and an actuator shaft that are configured to deploy the fastener as either a knot replacement or a knot pusher. The closure device is also configured to trim the sutures after deployment. The closure device may include cutters formed or included in the outer and actuator shafts that are configured to trim the sutures by relative movement of the outer and actuator shafts.

In another embodiment, a closure device for closing an opening in tissue is provided. The closure device includes an actuator shaft and an outer shaft. The actuator shaft is configured to move slidably within the outer shaft. Each of the outer shaft and the actuator shaft has an opening formed therein with a cutter. Relative movement of the outer and actuator shafts causes the cutters to trim the sutures. The outer shaft includes a recess that is configured to removably receive a fastener. Distal movement of the actuator shaft relative to the outer shaft dislodges the fastener from the recess.

In another embodiment, a method for closing an opening in tissue is provided. The method includes loading a closure device with a fastener. When loading the closure device, sutures are drawn through the fastener and through an opening a sidewall of the closure device. Then, the fastener is deployed from the closure device and the sutures are trimmed at the opening in the sidewall of the closure device.

BRIEF DESCRIPTION OF THE DRAWINGS

To further clarify at least some of the advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. Embodiments of the invention will be described and explained with additional specificity and detail through the use of the accompanying drawings in which.

DETAILED DESCRIPTION OF THE PREFERRED EMBODIMENTS

Figure 1:
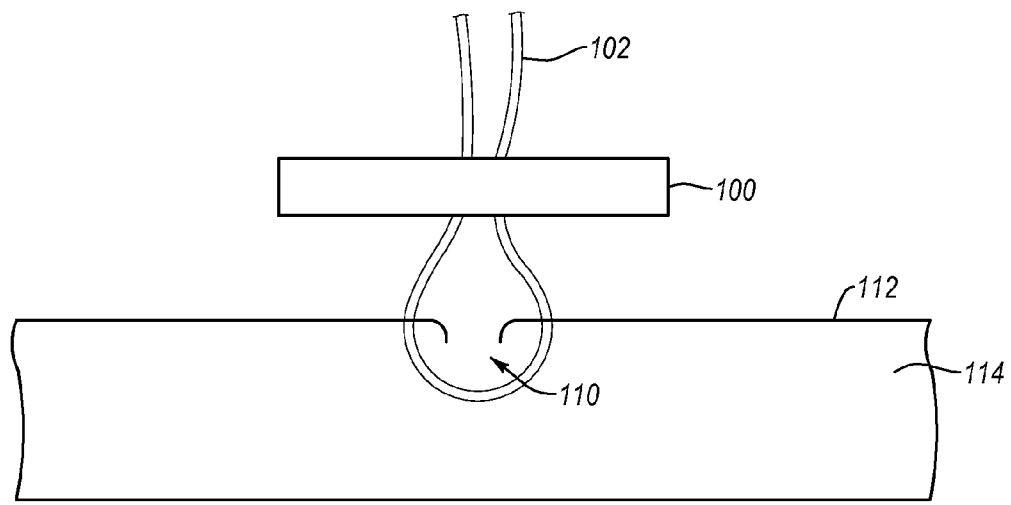
FIG. 1 shows an illustrative embodiment of a fastener that can be implemented as a knot pusher or a knot replacement device and used in closing an opening in tissue.

Systems, devices, and methods are disclosed herein for managing access to body lumens through tissue, including management of openings in the tissue. Embodiments disclosed herein more specifically relate to closing openings or holes in the body tissue. Several examples are described below in which a fastener may be deployed to close or substantially close (or aid in closing) a hole through which access to a body lumen is achieved. Some embodiments may be used or aid in closing and/or substantially closing openings in a blood vessel or other tissue formed during a diagnostic, therapeutic, and/or other procedure.

Closure of a hole in tissue (e.g., an arteriotomy) is often a process that is accomplished by performing a few steps. Generally, sutures are first placed around the arteriotomy. The sutures are typically placed in the vessel wall immediately surrounding or adjacent or proximate the arteriotomy. The sutures can be placed in the vessel's walls before and/or after any procedure that may be performed through the arteriotomy. After the procedure is completed or after the sutures are placed, the sutures are cinched together and locked in place to close the opening and allow healing to occur.

Embodiments of the invention include a closure system capable of closing the opening using a fastener. The fastener can be used as a knot pusher and/or as a knot replacement. Embodiments of the invention relate to a closure device that can operate as a knot pusher/suture cutter and/or a knot replacement/suture cutter. Advantageously, multiple persons (e.g., physician or nurse) can use the same device to close an opening in tissue in different ways. One person may use the closure system as a knot pusher while another person may use the closure system as a knot replacement. In both cases, the closure system may also be configured to cut or trim the sutures after deployment of the fastener to push the knot or as a knot replacement.

Embodiments of the closure system disclosed herein include a deployment or closure device and a fastener. The closure device includes an outer shaft and an actuator shaft. The actuator shaft may be configured to be displaced proximally and distally relative to the outer shaft. The actuator shaft is slidably disposed inside the outer shaft.

A fastener can be placed and held in a distal end of the outer shaft of the closure device. When the closure device is operating as a knot pusher, the sutures are threaded through the fastener or otherwise engaged with the fastener after a pushable knot has been tied in the sutures. The sutures may also be threaded through an opening in a sidewall of both the actuator shaft and the outer shaft. The outer shaft or the actuator shaft can then be used to push on the fastener, which in turn pushes the knot to cinch the sutures and lock the sutures in place.

The fastener is pushed towards the opening without displacing the actuator shaft relative to the outer shaft in one embodiment. Because the openings in the sidewalls of the outer shaft and the actuator shaft may be configured as cutters, the sutures can be cut or trimmed by moving the outer shaft relative to the actuator shaft.

The following discussion refers to a vessel and to openings that may be formed in the vessel's wall such as an arteriotomy. One of skill in the art, with the benefit of the present disclosure, can appreciate that embodiments of the invention can be used to close or substantially close gaps, discontinuities, or other openings in tissue in addition to vessels.

FIG. 1 shows an illustrative embodiment of a fastener 100 that is configured to close or aid in closing openings in tissue. FIG. 1 illustrates an opening 110 in tissue, such as a vessel 112. The opening 110 (e.g., an arteriotomy) may often be formed during a diagnostic, therapeutic and/or other procedure to access a body lumen 114. Once the procedure is finished, the opening 110 is usually at least partially closed.

In this example, sutures 102 are used to close the opening 110. The sutures 102 are placed in the walls of the vessel 112 proximate the opening 110. In this example, the sutures 102 surround the opening 110 and are drawn through the fastener 100. In other examples, the sutures may be placed at various locations about or proximate the opening 110. The fastener 100, after the sutures 102 are drawn tight or cinched, can lock the sutures 102 in place while holding the opening 110 closed, allowing the opening 110 to heal. As previously stated, locking the sutures 102 in place can include pushing a knot towards the opening 110 or deploying the fastener 100 as a knot replacement. FIG. 1 illustrates the fastener 100 as a knot replacement. No knot is formed in the sutures 102 and the fastener 100 operates to prevent the sutures 102 from loosening. The sutures 102 may be locked in place by securing or holding the sutures 102 in the fastener 100 as described in more detail below. The sutures can be held by friction or by deforming the knot replacement or the like.

Figure 2A:
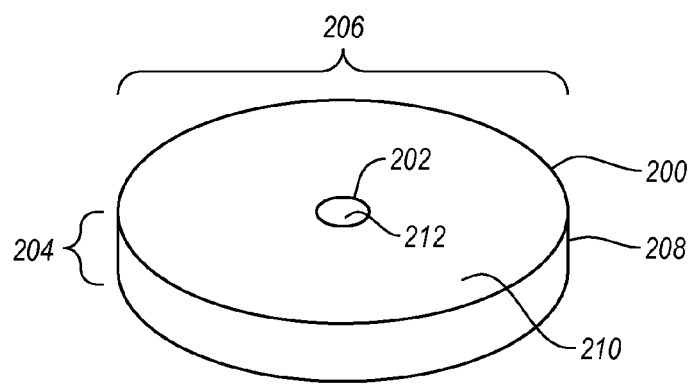
FIG. 2A shows an illustrative embodiment of the fastener shown in FIG. 1.
Figure 2B:
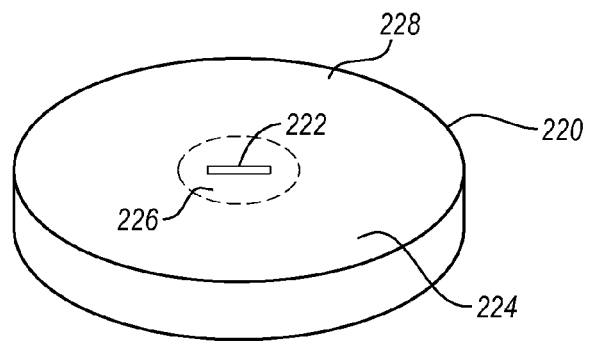
FIG. 2B shows another illustrative embodiment of the fastener shown in FIG. 1.
Figure 2C:
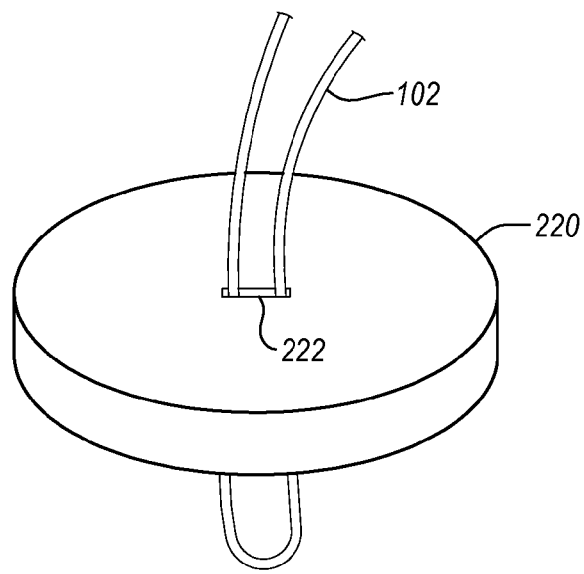
FIG. 2C shows the fastener of FIG. 2B engaged with sutures.
Figure 2D:
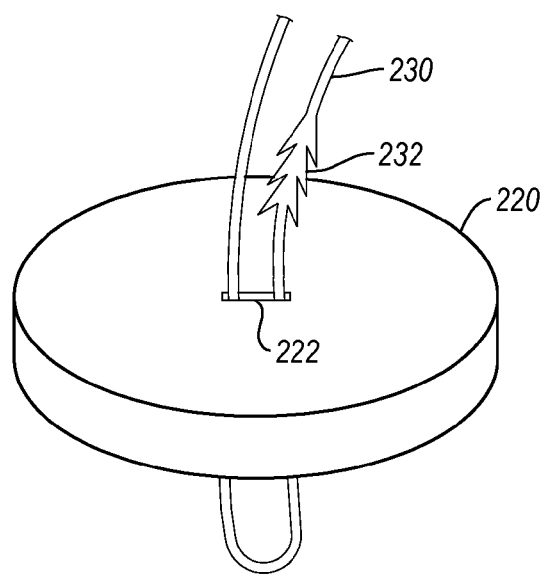
FIG. 2D shows the fastener of FIG. 2B engaged with sutures that include a prepared surface to operate in conjunction with the fastener.

FIGS. 2A-2D illustrate various embodiments of a fastener. FIG. 2A shows an illustrative embodiment of a fastener 200. FIG. 2B shows another illustrative embodiment of a fastener 220. FIG. 2C illustrates the fastener of FIG. 2B clamping sutures. FIG. 2D illustrates the fastener of FIG. 2B using sutures that are configured to engage with the fastener 220. The fasteners 200 and 220 are examples of the fastener 100 illustrated in FIG. 1.

The fastener 200 illustrated in FIG. 2A can be used as a knot pusher and/or as a knot replacement to close the opening 110 in the vessel 112. The fastener 200 includes a body 210 and an opening 202. The sutures 102 can be drawn through the opening 202 using, for example, a snare device. Once the sutures 102 are drawn through the opening 202, the fastener 200 can be deployed to close or to aid in closing the opening 110.

The fastener 200 has a body 210 with dimensions or shape including a thickness 204, a width 206 and a perimeter 208. The fastener 200 or the body 210, by way of example and not limitation, may have a diameter of approximately 10 mm. The diameter may be smaller, for example, on the order of 5 mm or 3 mm. Smaller dimensions are also possible. A thickness of the body 210, by way of example only, may be about 5 mm or smaller such as 4 mm or 3 mm or smaller. The arrangement or configuration of the dimensions of the body 210 can vary. The perimeter 208, for example can be circular, elliptical, polygonal or other shape. The perimeter and/or other dimensions of the fastener 200 may be symmetrical or asymmetrical. The width 204 may be greater than, equal to, or less than the width 206. A cross section of the body 210 may be rectangular, elliptical, cone-shaped, polygonal, or the like. Interior walls 212 of the opening 202 may be smooth, roughened, jagged, or the like. The walls 212 may be configured to engage and hold the sutures 102 in order to lock the sutures 102 in place. The width 204 may be configured to exert a certain force on the opening 202 to securely hold the sutures 102. For example, the size or dimensions of the opening 202 and/or the width 204 of the fastener 200 may be selected according to the number of sutures 102 to be held and/or the corresponding dimensions of the sutures 102 and/or the type of sutures 102. This ensures that, for a given situation, the appropriate fastener may be selected.

The opening 202 may have dimensions that accommodate a predetermined number of sutures. For example, when the fastener 200 is used as a knot pusher, the opening 202 may be sized to permit the passage of a predetermined number of sutures while preventing the passage of a knot formed in the sutures. As a result, distal movement of the fastener 200 pushes or advances a pushable knot towards the opening 110 when closing the opening 110.

When the fastener 200 functions as a knot replacement, the opening 202 may be configured to frictionally (or otherwise) engage the sutures 102 in a manner that prevents the fastener 200 from sliding along the sutures 102 or otherwise becoming displaced in the absence of sufficient force. As a result, a force can be applied to the fastener 200 to cinch the sutures 102 and deploy the fastener 200 towards the opening 110. When the deployment force is removed, the opening 202 or more generally the fastener 200 is sufficiently engaged with the sutures 102 to prevent displacement of the fastener 200 and prevent the sutures 102 from loosening at least until the opening is sufficiently healed or until any other appropriate time.

In one example, the body 200 is formed of a relatively inelastic material. When the fastener 200 is used to push a knot, the relative inelasticity of the fastener 200 ensures that the knot is pushed towards the opening 110 and does not pass through the opening 202. In this example, the dimensions of the knot are larger than the dimensions of the opening 202 and the knot will not pass into the opening 202 during the procedure of closing the opening 110 with a knot.

The fastener 200 may also hold the sutures 102 by friction and operate as a knot replacement. In this example, the size of the opening 202 is selected such that the sutures 102 have a tight fit when drawn through the opening 202. The tight fit can be overcome to deploy the fastener 200, but exerts sufficient force to prevent the sutures 102 from slipping or loosening.

In another example, the fastener 200 can also be crimped and plastically deformed to hold the sutures 102 in place. In this example, the opening 202 is effectively closed on the sutures 102 to clamp the sutures 102 in place.

FIG. 2B illustrates another example of a fastener 220. The fastener 220 may have dimensions like or similar to the dimensions and shape of the fastener 200. Many of the dimensions of the fastener 200 may also apply to the fastener 220. In this example, however, a body 224 of the fastener 220 is more elastic than the body 210 of the fastener 200. Alternatively, a portion 226 of the body 224, surrounding an opening 222, may be more elastic or flexible than the rest of the body 224 such as the portion 228.

In this example, the opening 222 may be formed as a slit in the body 224 or in the portion 226. Because the body 224 (or portion thereof) is relatively more elastic compared to the fastener 200, the opening 222 may elastically deform sufficiently to allow the sutures 102 to be drawn through the opening 222. The elastic force or aspect of the body 224 applies a force on the sutures 102 to lock the sutures 102 in place. The sides or walls of the opening 222 press against the sutures 102 to hold the sutures in place, for example by friction. The friction can be overcome when deploying the fastener 220 but is sufficient to keep the fastener 220 in place and securely hold the sutures 102 in place after deployment.

FIG. 2C illustrates an example of the fastener 210 engaged with the sutures 102 and holding the sutures 102 in place. As shown in FIG. 2C, the sides of the opening 222 press against the sutures 102 to hold the sutures 102 in place after the fastener 210 is deployed. A larger width may increase the force with which the sutures 102 are held.

FIG. 2D illustrates the fastener 220 that is configured to hold or secure sutures 230. In this example, the sutures 230 include a prepared surface or area 232 that is configured to engage with the fastener 220. The prepared area 232 may include barbs or other feature that are oriented such that the sutures 230 pass through the opening 222 in one direction easier than the other direction. When closing the opening 110, the prepared area 232 may be oriented such that once the fastener 220 can be pushed distally towards the opening 110. The prepared area 232 inhibits or prevents the fastener 220 from moving proximally. When properly deployed, the prepared area 232 may be located in the opening 222. Thus, the sutures 230 are positioned prior to deployment of the fastener 220. In addition to barbs, the prepared area 232 may be roughened, coated with an adhesive, or otherwise prepared to engage the fastener 220 to lock the sutures 230 in place with the opening 110 closed.

The fastener 220 (or the fastener 200) may hold the sutures 102, or 230 in place by friction, adhesive, and/or structural impediment (e.g., a roughened surface or barbed surface).

The opening 202 or 222 may also be configured to extend to the perimeter of the fastener. Thus, the sutures can be loaded into the fastener through the side of the fastener rather than having to use a snare to draw the sutures through the opening. The patch formed by the opening may be a straight line, or include curves, or other path with sharper corners.

Figure 3A:
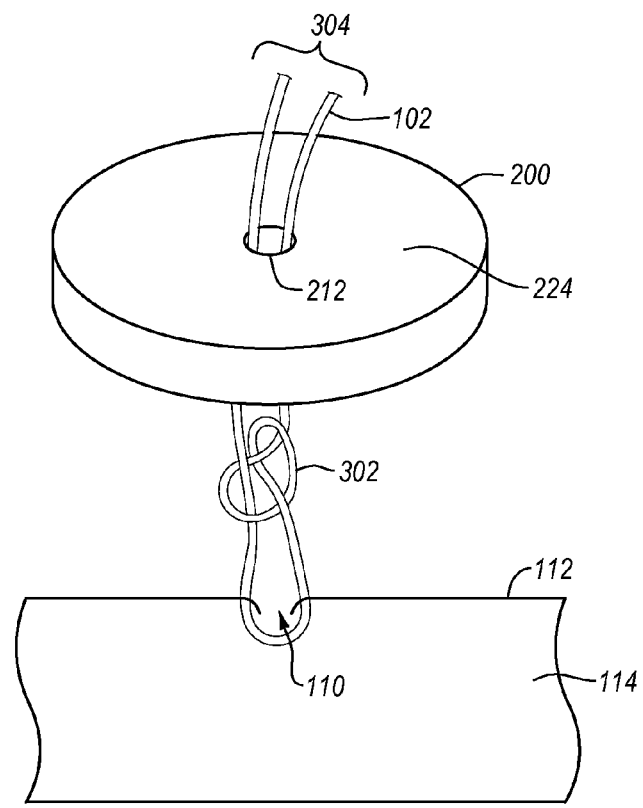
FIG. 3A shows the fastener of FIG. 2A operating as a knot pushing closure device to close an opening in tissue.

FIG. 3A illustrates the fastener operating as a knot pusher. In this example, a pushable or movable knot 302 has been formed in the sutures 102. Ends 304 of the sutures 102 (which may be color coded to aid in closing the opening to allow the physician to know on which end to pull) are drawn through the opening 202. The opening 202, which is typically sized such that the knot 302 cannot enter therein, or more specifically the body 224 proximate the opening 202 can then push the knot 302 towards the opening 110 during deployment of the fastener 200. Once the fastener 200 has pushed the knot such that the sutures 102 are cinched tight and the opening 110 remains closed, the fastener 200 can be removed.

Figure 3B:
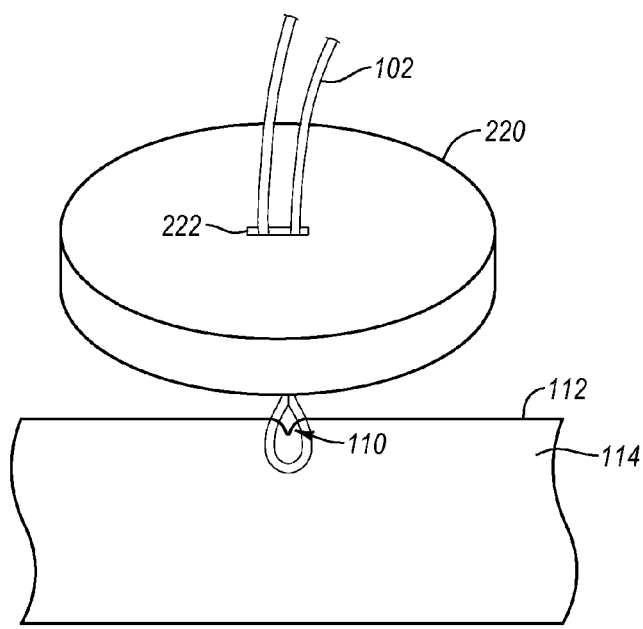
FIG. 3B shows the fastener of FIG. 2B operating to close an opening in tissue.

FIG. 3B illustrates the fastener operating as a know replacement. In FIG. 3B, the fastener 210 is pushed distally towards the opening 110 after the sutures 102 are drawn through the opening 222. When finally deployed and after the sutures 102 are cinched, the opening 222 or body of the fastener 220 engages the sutures 102 with sufficient force to prevent the sutures 102 from loosening. As previously stated, the opening 222 may have a frictional fit with the sutures 102 that holds the sutures 102 in place long enough for healing to occur at the opening 110. The opening 222 may also have engage the sutures with an adhesive or with structure. The interior walls (e.g., walls 212 in FIG. 2A) of the opening 222 (or of the opening 202) may be roughened to improve the frictional force or have impeding structure that is configured to facilitate movement of the fastener in the distal direction and impede movement of the fastener in the proximate direction. The sutures 102 may have similar impeding structure as previously described.

Figure 4:
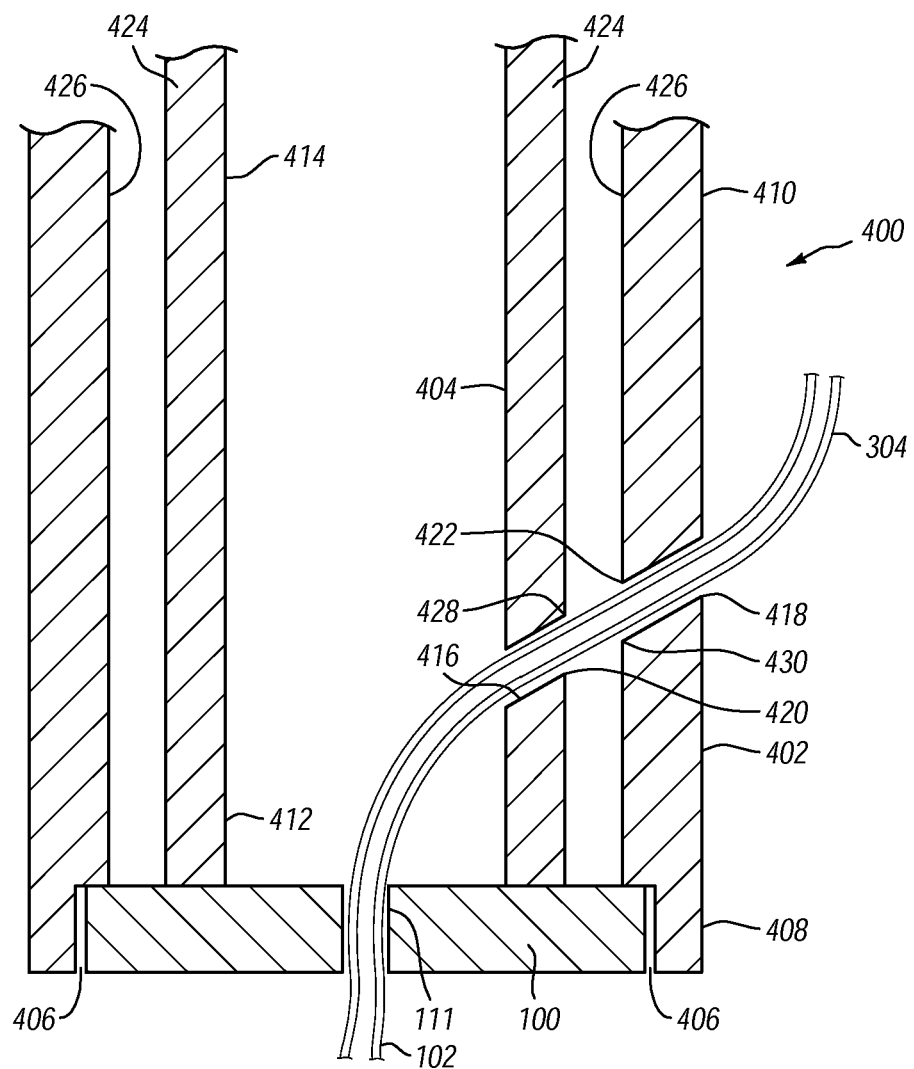
FIG. 4 shows an illustrative embodiment of a closure system that includes a closure device for deploying a fastener.

FIG. 4 shows an illustrative embodiment of a closure system that includes a closure device 400 and the fastener 100. The closure system can act or operate as either a knot pushing system or a knot replacement system. The closure device 400 includes an outer shaft 402 with a proximal end 410 and a distal end 408. The outer perimeter, inner perimeter, and/or cross-sectional shape of the outer shaft 402 can be circular, polygonal, or other shape.

The closure device 400 also includes an actuator shaft 404 with a proximal end 414 and a distal end 412. The outer perimeter, inner perimeter, and/or cross-sectional shape of the actuator shaft 404 can be circular, polygonal, or other shape. The actuator shaft 404 can be moved in both distal and proximal directions relative to the outer shaft 402. Similarly, the outer shaft 402 can be moved in both distal and proximal directions relative to the actuator shaft 404. The outer shaft 402 and the actuator shaft 404 can be moved at the same time or separately. The actuator shaft 404 is typically configured to slidably reside inside the outer shaft 402. In one example, an outer perimeter or surface 424 of the actuator shaft 404 is in contact with an inner perimeter or surface 426 of the outer shaft 402. The friction between the outer surface of the actuator shaft 404 and the inner surface of the outer shaft 402 may be sufficient to prevent inadvertent movement but also enable a user to operate the closure device 400 and achieve relative movement between the actuator shaft 404 and the outer shaft 402.

During operation of the closure system, the fastener 100 is placed or loaded in a recess 406 formed in the distal end 408 of the outer shaft 402. The recess 406 is typically sized and configured to hold the fastener 100. The recess 406 may be configured such that a surface of the fastener 100 extends out of the recess, is flush with the edge of the recess or is inside of the recess. The fastener 100 may engage the recess with sufficient friction to enable the closure device 400 to deploy the fastener 100 while retaining the fastener 100 within the recess 406 until the fastener 100 is positively expelled or discharged by the user. For example, distal movement of the actuator shaft 404 relative to the outer shaft 402 can dislodge or expel the fastener 100 from the recess 406.

After (or before in some embodiments) the fastener 100 is loaded in the recess 406, the sutures 102 are drawn through the opening 402 (which is an example of the openings 212 and 222) of the fastener 100 and through the openings 416 and 418, respectively, in the sidewalls of the actuator shaft 404 and the outer shaft 402. The openings 416 and 418 are initially aligned such that the sutures 102 can be drawn through them when preparing the closure system. When the outer shaft 402 and the actuator shaft 404 are non-circular or have a cross section that is not a circle, it is easier to maintain alignment of the openings 416 and 418. For example, hexagonally shaped outer and actuator shafts 402 and 404 can provide proper alignment for the openings 416 and 418 as well as ensure that the alignment is maintained during use of the closure device 400. In another example, the outer shaft 402 and the actuator shaft 404 may have a tongue and groove arrangement (another example of a non-circular arrangement) to keep the shafts aligned as discussed herein.

More specifically, the inner cross section of the outer shaft 402 and the outer cross sectional shape of the actuator shaft 404 may be the same to as to allow for relative movement in the distal and proximal directions while allowing the openings 416 and 418 to be aligned using only proximal and distal movement of the outer and/or actuator shafts rather than rotational movement of the actuator shaft 404 relative to the outer shaft 402. In other words, the outer shaft 402 and the actuator shaft are configured to allow for distal and proximal movement but not relative rotational movement in one embodiment.

FIG. 4 illustrates that the closure device 400 and the fastener 100 can be used as a knot pusher. When used as a knot pusher, a sliding knot is formed in the sutures 102 before the sutures 102 are drawn through the opening 402 and the openings 416 and 418. The outer shaft 402 and the fastener 100 can then be used to push the knot to the opening 110. Distal movement of the outer shaft 402 translates to distal movement of the fastener 100, which in turn pushes the knot distally towards the opening 110. Often, the actuator shaft 404 is moved distally as well when the closure device is also configured to trim the sutures 102 to prevent the sutures 102 from being trimmed prematurely. In one example, the closure device 400 may include a lock that prevents relative movement until the lock is released by the user.

The opening 402 is sized such that the knot does not pass through the opening 402. When the sutures 102 are cinched tight and the sutures 102 are locked such that the opening 110 in the vessel or other tissue is closed or substantially closed, the actuator shaft 404 can be moved proximally. When the actuator shaft 404 is moved proximally relative to the outer shaft 402, a cutter 420 formed in the actuator shaft 404 may engage with a cutter 422 formed in the outer shaft 402 to cut or trim the sutures. In other words, the sutures 102 can be cut or trimmed by a scissor action between the actuator shaft 404 and the outer shaft 402. After the procedure or after the know is pushed, the closure device 400, including the fastener 100 which is still lodged in the recess 406, can be withdrawn.

In an alternative example, the closure device 400 deploy the fastener 100 as a knot replacement. In this example, the sutures 102 are drawn through the opening 402 and through the openings 416 and 418. The sutures 102 can be cinched tight to close the opening 110 and the actuator shaft 404 can be moved distally to dislodge the fastener 100 from the outer shaft 402. The distal movement of the actuator shaft 404 can be performed to push the fastener 100 distally while holding on to the ends 304 of the sutures 102 and/or a proximal end of the outer shaft 402. This ensures that the sutures 102 remain tight until the fastener 100 is properly placed adjacent the opening in the tissue.

For example, the outer shaft 402 can be used to place the fastener 100 against the opening 100. In this case, the actuator shaft 404 is held against the fastener 100 while the outer shaft 404 is moved proximally. The effect is that the fastener 100 is dislodged from the distal end 408 of the outer shaft 402. In this example, the fastener 100 may frictionally or otherwise engage the sutures 102 as described herein such that the sutures 102 are held in place and the opening 110 remains closed.

The opening 111 is sized such that the knot does not pass through the opening 111. When the sutures 102 are cinched tight and the sutures 102 are locked such that the opening 110 in the vessel or other tissue is closed or substantially closed, the actuator shaft 404 can be moved proximally. When the actuator shaft 404 is moved proximally relative to the outer shaft 402, a cutter 420 formed in the actuator shaft 404 may engage with a cutter 422 formed in the outer shaft 402 to cut or trim the sutures. In other words, the sutures 102 can be cut or trimmed by a scissor action between the actuator shaft 404 and the outer shaft 402. After the procedure or after the knot is pushed, the closure device 400, including the fastener 100 which is still lodged in the recess 406, can be withdrawn.

The cutters 420 and 422 can be formed in sidewalls of the outer shaft 402 and the actuator shaft 404. The cutters 420 and 422 can be arranged such that distal and/or proximal movement of the actuator shaft 404 (or of the outer shaft 402) trims the sutures 102, for example, with a scissor effect. In one example, the openings 416 and 418 may have a trapezoidal shape to aid in the scissor effect in both proximal and distal directions. For example, the actuator shaft 404 and the outer shaft 402 may be configured such that the sutures 102 are cut in the opposite direction using the edges 428 and 430. When the openings 416 and 418 are trapezoidal, the edges 428 and 430 have a scissor like arrangement with respect to lone another like the cutters 420 and 422. In one example, the sutures 102 could be trimmed at the same time that the fastener 100 is dislodged from the outer shaft 402. Thus, distal movement of the actuator shaft 404 can expel the fastener 100 from the outer shaft 402 and trim the sutures 102 at substantially the same time.

Figure 5:
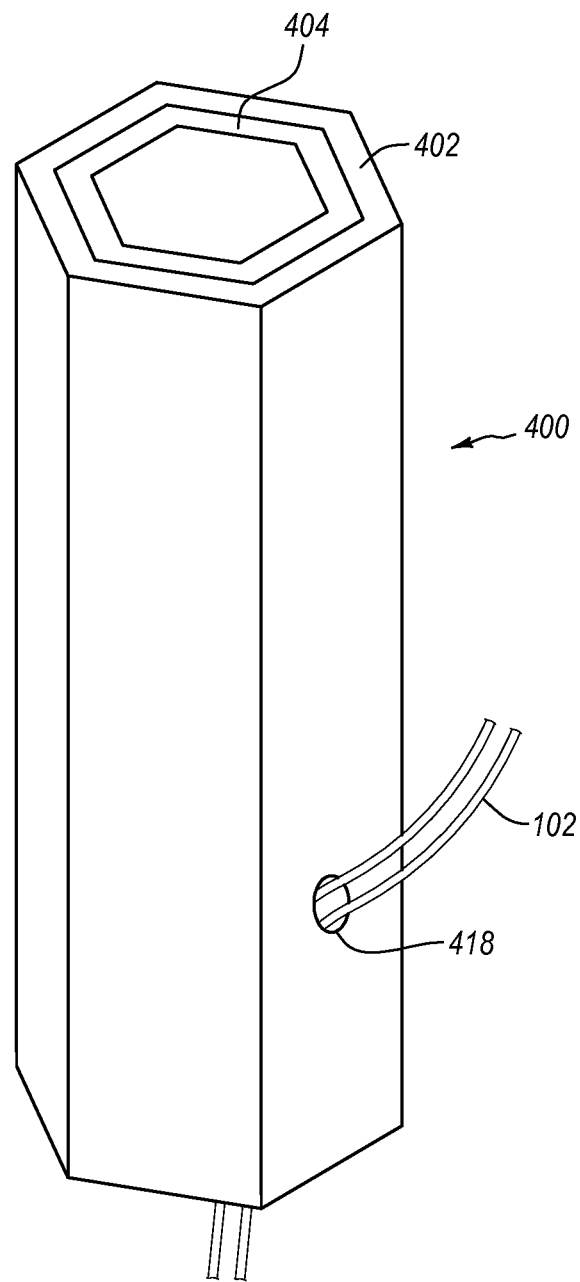
FIG. 5 shows a perspective view of the closure device shown in FIG. 4.

FIG. 5 shows a perspective view of the closure device 400. The closure device 400 illustrates that the actuator shaft 404 and the outer shaft 402 are configured to be slidably displaced relative to each other. The actuator shaft 404 may be in contact with the outer shaft 402. The contact between the actuator shaft 404 and the outer shaft 402 aids in the scissor action that trims the sutures as previously described. Alternatively, the closure device 400 may be configured such that a space is present between the actuator shaft 404 and the outer shaft 402. A space may facilitate relative movement while still preventing relative rotational movement between the actuator shaft 404 and the outer shaft 402. The space may be small enough to not interfere with the ability of the closure device 400 to trim or cut the sutures. FIG. 5 further illustrates that the sutures exit the closure system through the openings 418. Thus, the sutures 102 can be grasped by a user of the closure system as necessary to either tighten the sutures and/or deploy the fastener as a knot pusher or a knot replacement. FIG. 5 also illustrates a lock 502 located, in this example at a proximate end of the closure device 400. The lock 502 may be configured to engage with both the outer shaft 402 and the actuator shaft 404 to prevent relative movement between them.

Figure 6:
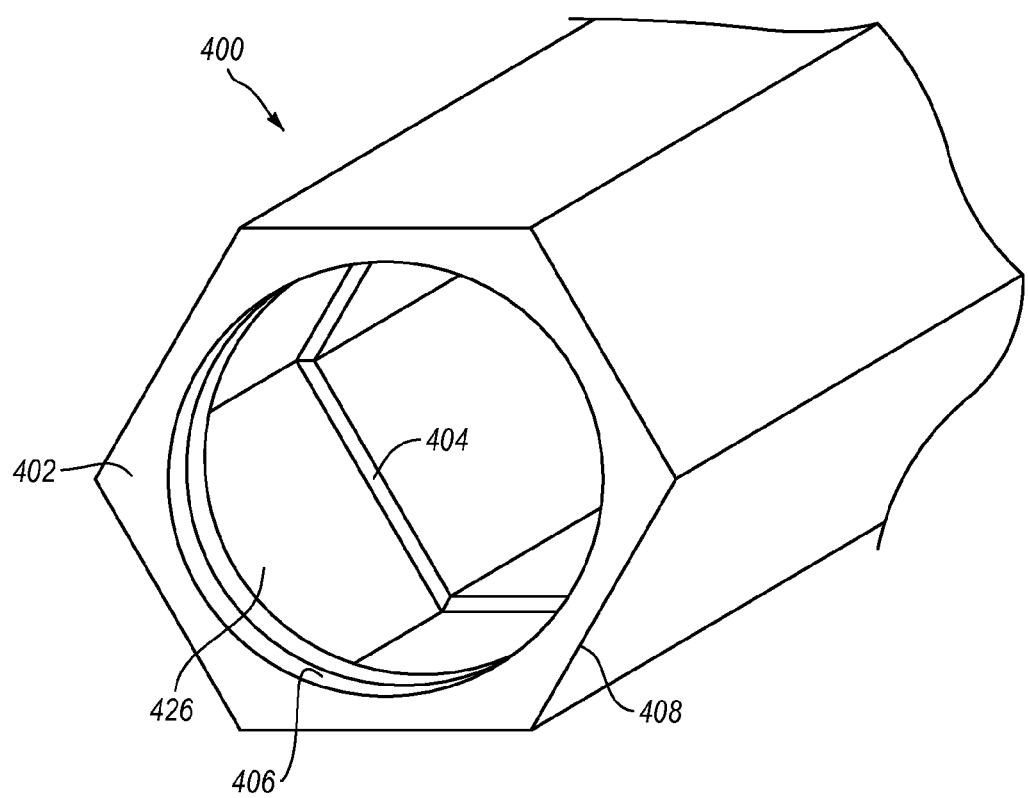
FIG. 6 shows an end view of a distal end of the closure device shown in FIG. 4.

FIG. 6 illustrates a perspective view of the distal end of the closure device 400. FIG. 6 illustrates that the recess 406 may be circular in shape while the interior surface 426 may have another shape (e.g., hexagonal or other shape that prevents relative rotational movement between the outer and actuator shafts). This enables the fastener 100 to be more easily loaded into the recess 406 and still enable the openings 416 and 418 to be easily aligned. FIG. 6 further illustrates that the actuator shaft 404 is proximally withdrawn.

The recess 406 may be configured with a ridge or other retaining mechanism that operates to retain the fastener 100 in the recess 406. The effect of the retaining mechanism can be overcome and the fastener 100 dislodged by proximal and/or distal translation of the actuator shaft 404 relative to the outer shaft 402. In one example, the retaining mechanism includes dimensions that are sufficiently smaller than the dimensions of the fastener 100 to achieve a frictional fit. In another embodiment, the fastener 100 may be configured with a complementary structure that removably engages with the recess 406 to retain the fastener 100 in the recess until the fastener 100 is positively dislodged by a user. For example, the recess 406 may include a lip structure that engages with a groove formed on in the fastener 100.

Figure 7:
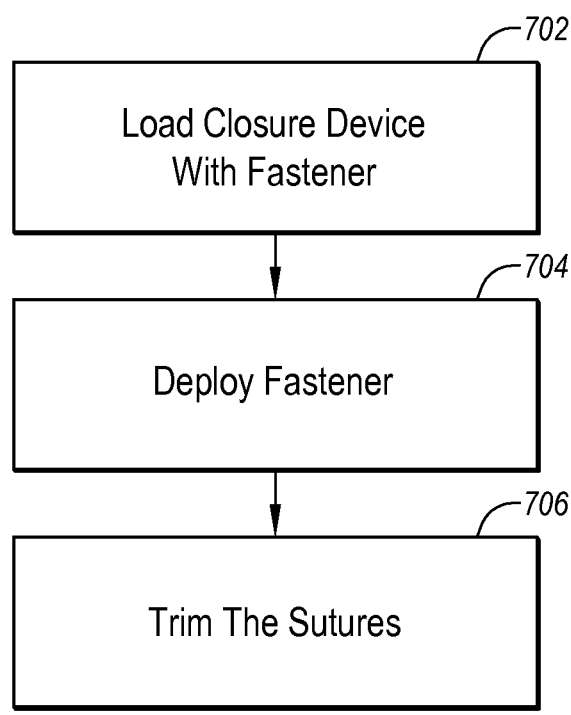
FIG. 7 shows an illustrative example of a method for closing an opening in tissue.

FIG. 7 illustrates an example of a method for closing an opening in tissue. The method may begin in box 702 by loading a closure device with a fastener. Loading the closure device can include drawing the sutures through the fastener as well as through the openings formed in the sidewalls of the actuator and outer shafts of the closure device. Loading the closure device also include placing the fastener in the recess formed in the distal end of the closure device. When operating as a knot pusher, a knot is formed in the sutures. In addition, one of skill in the art can appreciate that the sutures are typically placed in the tissue prior to loading the closure device.

In box 704, the fastener is deployed. Deploying the fastener can include moving the closure device in a distal direction to push the fastener (and thus the knot when operating as a knot pusher) towards the opening in the tissue. Once the fastener is adjacent the opening and the sutures are tightened, the suture can be dislodged by advancing the actuator shaft distally relative to the outer shaft. The distal end of the actuator shaft presses against the fastener and pushes the fastener out of the distal end of the outer shaft. In one example, the actuator shaft may be held stationary while the outer shaft is moved proximally.

In box 706, the sutures are trimmed. Because the sutures are threaded through openings in the sidewalls of the closure device, which openings are configured with one or more cutters, the sutures can be trimmed by relative movement of the outer and actuator shaft. By way of example only, the sutures can be trimmed when the fastener is dislodged from the distal end of the outer shaft. Alternatively, the sutures can be trimmed by moving the actuator shaft proximally after the fastener is properly placed.

Embodiments of the closure system (e.g., the closure device, fastener, or elements thereof) included therein may be made of any suitable material, including a bioabsorbable, biodegradable, or bioerodable material. Such materials may include polycaprolactone (PCL), poly(D, L-lactic acid), Poly-L-Lactic acid, poly (lactide-co-glycolide), poly(hydroxybutyrate), polyanhydrides, poly(glycolic acid, other bioabsorbable or biodegradable materials or combos thereof.

At least a portion of the closure device (e.g., that forms the cutting edges or the material defining the openings 416 and 418) is formed of a material capable of trimming the sutures.

The closure system disclosed herein (can be comprised of a variety of known suitable materials, including stainless steel, silver, platinum, tantalum, palladium, nickel, titanium, nitinol, nitinol alloys having tertiary materials, niobium-tantalum alloys optionally doped with a tertiary material, cobalt-chromium alloys, or other known biocompatible materials. Such biocompatible materials can include a suitable biocompatible polymer in addition to or in place of a suitable metal. A device or member can include biodegradable, bioerodable, or bioabsorbable materials.

In one embodiment, the closure device or fastener can be made at least in part of a high strength, low modulus metal alloy comprising niobium, tantalum, and at least one element selected from the group consisting of zirconium, tungsten, and molybdenum. The materials composing the medical devices or members according to the present invention may provide superior characteristics with regard to bio-compatibility, radio-opacity and MRI compatibility.

Furthermore, the closure device body or other medical device, including the closure device, can be formed from a ceramic material. In one aspect, the ceramic can be a biocompatible ceramic that optionally can be porous. Examples of suitable ceramic materials include hydroxylapatite, mullite, crystalline oxides, non-crystalline oxides, carbides, nitrides, silicides, borides, phosphides, sulfides, tellurides, selenides, aluminum oxide, silicon oxide, titanium oxide, zirconium oxide, alumina-zirconia, silicon carbide, titanium carbide, titanium boride, aluminum nitride, silicon nitride, ferrites, iron sulfide, and the like. Optionally, the ceramic can be provided as sinterable particles that are sintered into the shape of a closure device or layer thereof.

Moreover, the closure device or fastener can include a radiopaque material to increase visibility during placement. Optionally, the radiopaque material can be a layer or coating any portion of the device or member. The radiopaque materials can be platinum, tungsten, silver, stainless steel, gold, tantalum, bismuth, barium sulfate, or a similar material.

It is further contemplated that the external surface and/or internal surface of the devices or members (e.g., exterior and luminal surfaces) as well as the entire body can be coated with another material having a composition different from the primary material. The use of a different material to coat the surfaces can be beneficial for imparting additional properties to the device or member, such as providing radiopaque characteristics, drug-reservoirs, and improved biocompatibility.

The closure device can also be formed frombiocompatible polymeric materials that can include a suitable hydrogel, hydrophilic polymer, hydrophobic polymer, biodegradable polymer, bioabsorbable polymer, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), poly-hydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like.

Accordingly, embodiments of the invention can include or be coated with a drug or beneficial agent, for example an antibiotic to improve the use of the closure device.

The invention is susceptible to various modifications and alternative means, and specific examples thereof have been shown by way of example in the drawings and are herein described in detail. It should be understood, however, that the invention is not to be limited to the particular devices or methods disclosed, but to the contrary; the invention is to cover all modifications, equivalents, and alternatives falling within the spirit and scope of the claims.

The invention is susceptible to various modifications and alternative means, and specific examples thereof have been shown by way of example in the drawings and are herein described in detail. It should be understood, however, that the invention is not to be limited to the particular devices or methods disclosed, but to the contrary; the invention is to cover all modifications, equivalents, and alternatives falling within the spirit and scope of the claims.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A closure device for closing an opening in tissue, the closure device comprising:
   hollow actuator shaft having a distal end, a first opening, and a first cutter formed in the first opening;
   an outer shaft having a second opening, and a second cutter formed in the second opening, wherein the actuator shaft is configured to move slidably within the outer shaft; and
   a recess formed in the distal end of the outer shaft and configured to removably receive a fastener having an opening, wherein the hollow actuator shaft includes a hollow interior channel that is aligned with the opening of the fastener so that a suture passing through the opening of the fastener and through the first and second openings extends through the hollow interior channel disposed between the opening in the fastener and the first and second openings of the hollow actuator shaft and the outer shaft, respectively;
   wherein positioning the distal end of the actuator shaft against the proximal surface of the fastener and proximal movement of the outer shaft relative to the actuator shaft dislodges the fastener from the recess, and
   wherein upon positioning the fastener within the recess formed in the distal end of the outer shaft and the distal end of the actuator shaft against the proximal surface of the fastener, the first opening partially overlaps the second opening in a longitudinal direction of the actuator shaft and the outer shaft.

2. The closure device of claim 1, wherein the fastener pushes a knot when sutures are passed through an opening formed in the fastener after tying a knot in the sutures, wherein the opening is sized to prevent the knot from passing through the opening.

3. The closure device of claim 1, wherein the fastener includes an opening formed therein, wherein the fastener replaces a knot in the sutures when the sutures are locked in the opening in the fastener.

4. The closure device of claim 3, wherein at least a portion of a body of the fastener proximate the opening has an elasticity configured to grip the sutures and hold the sutures in place after deployment of the fastener.

5. The closure device of claim 1, wherein distal or proximal movement of the actuator shaft causes the first cutter to engage with the second cutter to trim sutures that pass through the first opening and the second opening.

6. The closure device of claim 1, wherein the outer shaft and the actuator shaft each have a non-circular shape to prevent rotational movement of the actuator shaft relative to the outer shaft.

7. The closure device of claim 6, wherein the recess formed in the distal end of the outer shaft configured to removably receive a fastener is circular.

8. The closure device of claim 1, wherein the fastener is configured to engage the recess with a frictional fit.

9. The closure device of claim 1, wherein the fastener includes an opening, wherein an inner wall of the opening comprises an adhesive.

10. The closure device of claim 1, wherein the recess includes a lip structure that engages with a groove formed in the fastener to retain the fastener in the recess.

11. The closure device of claim 1, further comprising a lock at a proximal end of the closure device that engages with both the outer shaft and the actuator shaft to prevent relative axial movement therebetween.

12. A closure system for closing an opening in tissue, the closure system comprising:
    a flat shaped fastener having a height that is less than its width, the fastener having an opening, wherein sutures are received through the opening; and
    a closure device configured to deploy the fastener, the closure device including an outer shaft and an actuator shaft configured to selectively press against and deploy the fastener as either a knot replacement or a knot pusher, the closure device being further configured to trim the sutures after deployment of the fastener,
    wherein upon positioning the fastener within the recess formed in the distal end of the outer shaft and the distal end of the actuator shaft against the proximal surface of the fastener, the first opening partially overlaps the second opening in a longitudinal direction of the actuator shaft and the outer shaft, proximal and distal ends of each of the first opening and the second opening being inclined in the same direction towards a longitudinal axis of the outer shaft and the actuator shaft.

13. The closure system of claim 12, wherein the actuator shaft is slidably disposed inside the outer shaft.

14. The closure system of claim 13, wherein the outer shaft includes a first opening having a first cutter and the actuator shaft includes a second opening having a second cutter, wherein the sutures are drawn thorough the first and second openings such that distal or proximal movement of the actuator shaft relative to the outer shaft causes the first cutter and the second cutter to cut the sutures.

15. The closure system of claim 14, wherein the first opening and the second opening each have a trapezoidal shape so as to cut the sutures when the actuator shaft moves distally or when the actuator shaft moves proximally.

16. The closure system of claim 14, wherein the actuator shaft is hollow so as to include a hollow interior channel that is aligned with the opening of the fastener so that the sutures passing through the opening of the fastener and through the first and second openings of the hollow actuator shaft and outer shaft, respectively, extend through the hollow interior channel disposed between the opening in the fastener and the first and second openings of the hollow actuator shaft and the outer shaft, respectively.

17. The closure system of claim 12, wherein the actuator shaft and the outer shaft are shaped to prevent rotational movement of the actuator shaft relative to the outer shaft.

18. The closure system of claim 13, wherein the outer shaft has an inner perimeter with a non-circular shape and an outer perimeter of the actuator shaft has a corresponding non-circular shape that allows relative movement in distal and proximal directions.

19. The closure system of claim 13, wherein a body of the fastener comprises one or more of:
   an elastic material, wherein the body is configured to hold the sutures in place by friction; or
   an inelastic material, wherein the opening is configured to receive the sutures and prevent a knot from entering the opening when acting as a knot pusher.

20. The closure system of claim 12, wherein the flat shaped fastener has a cross-sectional shape that is non-circular.

\* \* \* \* \*